US008463393B2

(12) United States Patent
Strother et al.

(10) Patent No.: US 8,463,393 B2
(45) Date of Patent: Jun. 11, 2013

(54) IMPLANTABLE MEDICAL DEVICES HAVING A LIQUID CRYSTAL POLYMER HOUSING

(75) Inventors: Robert B. Strother, Willoughby Hills, OH (US); Geoffrey B. Thrope, Shaker Heights, OH (US)

(73) Assignee: Medtronic, Inc., Minneapolis, MN (US)

( * ) Notice: Subject to any disclaimer, the term of this patent is extended or adjusted under 35 U.S.C. 154(b) by 1661 days.

(21) Appl. No.: 11/473,682

(22) Filed: Jun. 22, 2006

(65) Prior Publication Data

US 2008/0033500 A1 Feb. 7, 2008

(51) Int. Cl.
*A61N 1/00* (2006.01)
(52) U.S. Cl.
USPC .......................................................... 607/61
(58) Field of Classification Search
USPC ................................................ 607/36, 37, 61
See application file for complete search history.

(56) References Cited

U.S. PATENT DOCUMENTS

| | | | | |
|---|---|---|---|---|
| 4,254,775 | A * | 3/1981 | Langer | 607/5 |
| 5,461,256 | A * | 10/1995 | Yamada et al. | 257/679 |
| 5,645,586 | A * | 7/1997 | Meltzer | 623/11.11 |
| 5,741,313 | A * | 4/1998 | Davis et al. | 607/36 |
| 5,873,899 | A | 2/1999 | Stutz, Jr. et al. | |
| 6,319,208 | B1 * | 11/2001 | Abita et al. | 600/561 |
| 6,505,077 | B1 * | 1/2003 | Kast et al. | 607/61 |
| 6,554,822 | B1 * | 4/2003 | Holschneider et al. | 604/892.1 |
| 6,643,552 | B2 * | 11/2003 | Edell et al. | 607/116 |
| 6,694,190 | B1 * | 2/2004 | Spelman et al. | 607/57 |
| 6,721,602 | B2 * | 4/2004 | Engmark et al. | 607/36 |
| 2002/0042634 | A1 * | 4/2002 | Bardy et al. | 607/36 |
| 2003/0040779 | A1 | 2/2003 | Engmark et al. | |
| 2003/0144707 | A1 * | 7/2003 | Ruben et al. | 607/37 |
| 2004/0225213 | A1 | 11/2004 | Wang et al. | |
| 2005/0277844 | A1 | 12/2005 | Strother et al. | |
| 2006/0009815 | A1 | 1/2006 | Boveja et al. | |

FOREIGN PATENT DOCUMENTS

WO WO 2004/041072 A2 5/2004

OTHER PUBLICATIONS

Modern Plastics Worldwide, Notables: 10 Waves of the future by Modern Plastics Editorial Staff, Sample molding in progress, Sep. 1, 2005.
www.flipchips.com, Tutorial 31—Jun. 2003, A survey of water level hermetic cavity chip scale packages for RF applications, George A. Riley, PhD.
www.foster-miller.com, Project Examples, Packaging for Implantable Electronics, Foster-Miller, Inc., Feb. 15, 2006.
www.machinedesign.texterity.com, Vacuum-formed films for fit and function, High-performance films can replace injection-molded plastics when space is at a premium, David Midgley, Welch Fluorocarbon Inc., Dover, N.H., Oct. 7, 2004.
www.devicelink.com, MPMN, May 2004, Liquid-Crystal Polymer Meets the Challenges of RF Power Packaging; The plastic air-cavity packages are hermetically sealed using a proprietary process, Susan Wallace.

(Continued)

*Primary Examiner* — Christopher D Koharski
*Assistant Examiner* — Roland Dinga
(74) *Attorney, Agent, or Firm* — Shumaker & Sieffert, P.A.

(57) ABSTRACT

An implantable medical device having a liquid crystal polymer (LCP) housing. Circuitry is positioned within the housing to perform a predefined function, such as generate a stimulation waveform, or pump a fluid, or turn on a motor, for example. The circuitry may include a power source, and the power source may be a rechargeable power source.

25 Claims, 14 Drawing Sheets

OTHER PUBLICATIONS www.flipchips.com. Advanced Packaging—Wafer-level Hermetic Cavity Packaging, originally published in Advanced Packaging Magazine, May 2004, by George A. Riley.

Boston Healthcare Research Service, David J. Edell, PhD, Feb. 15, 2006.

http://crisp.cit.nih.gov/ Abstract, High-Density Liquid Crystal Polymer Cochlear Electrodes, Scott S. Corbett, Jul. 1, 2000.

Reply to Written Opinion dated Nov. 13, 2008 for corresponding PCT Application PCT/US2007/014396 (13 pgs.).

Notification of Transmittal of International Preliminary Report on Patentability dated Jun. 26, 2009 for corresponding PCT Application PCT/US2007/014396 (7 pgs.).

European Search Report dated Mar. 1, 2010 for corresponding European Application 07796297.5-2305 (9 pgs.).

European Examination Report dated Apr. 23, 2012 for European Application No. 07796297.5, (4 pgs.).

Response to Communication dated Jul. 3, 2012 for European Application No. 07796297.5, (4 pgs.).

* cited by examiner

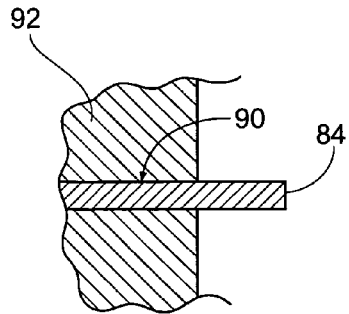
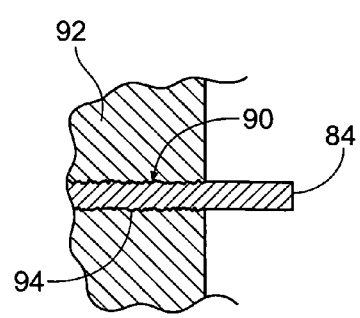
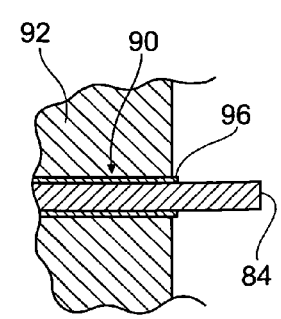
Fig. 8A     Fig. 8B     Fig. 8C
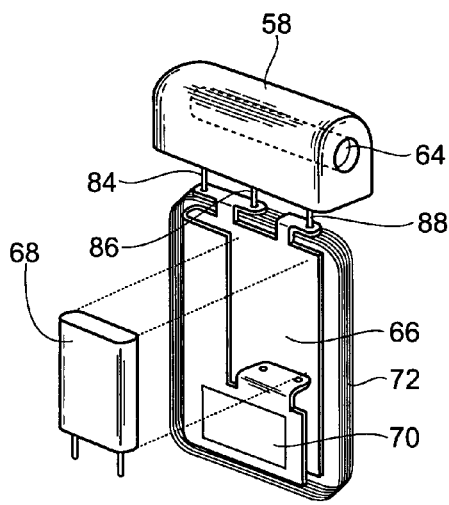
Fig. 9
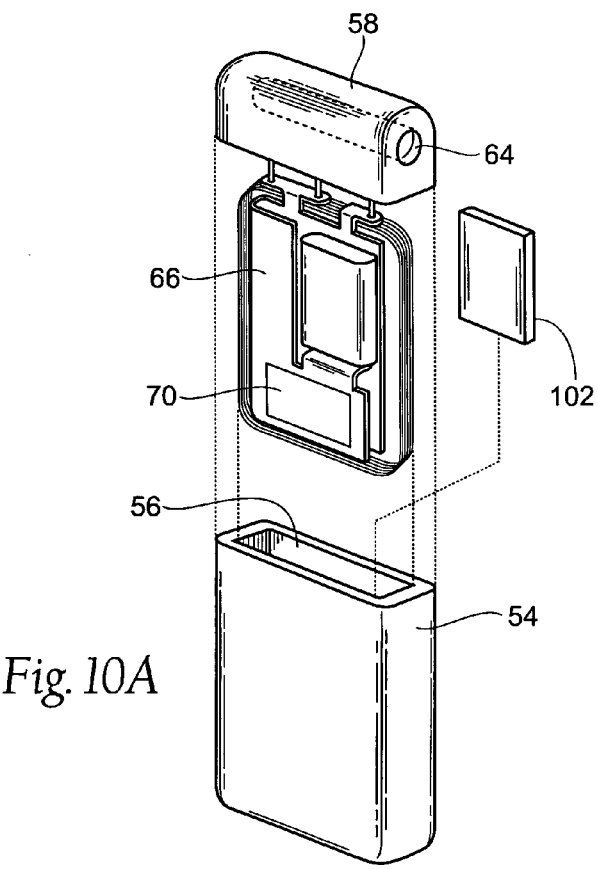
Fig. 10A

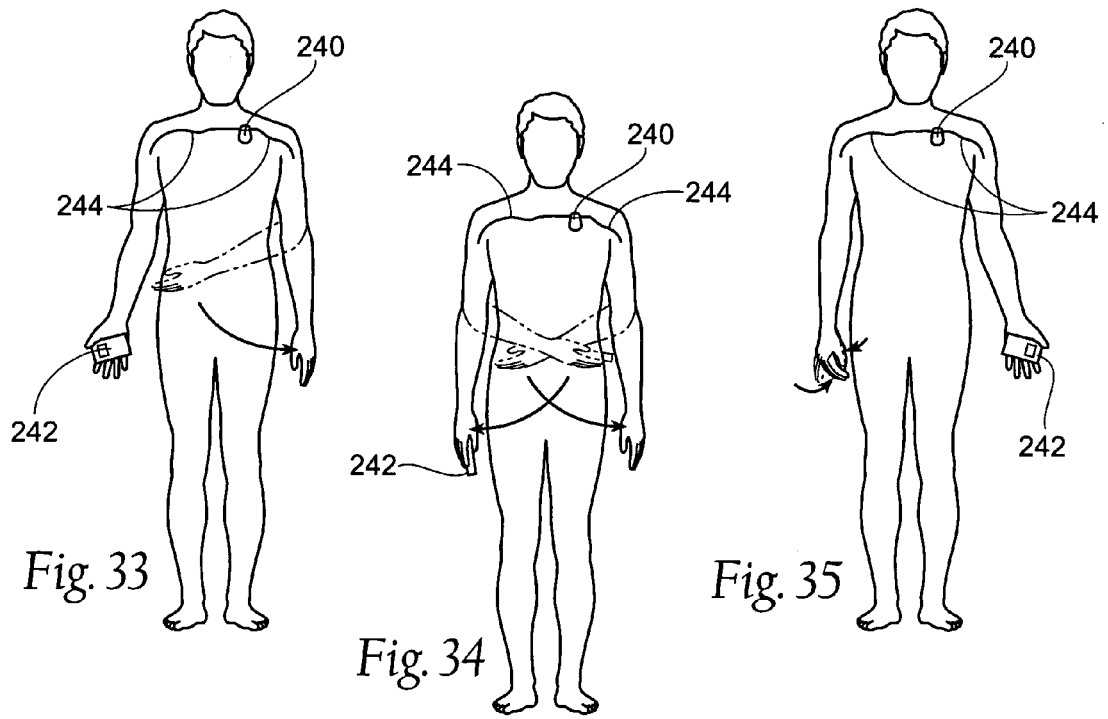
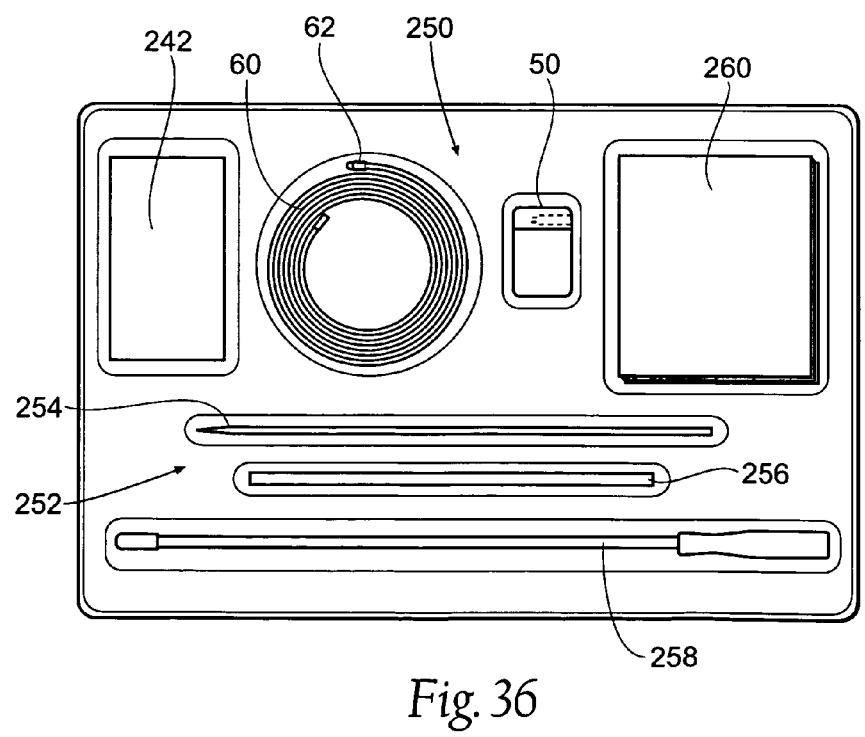

IMPLANTABLE MEDICAL DEVICES HAVING A LIQUID CRYSTAL POLYMER HOUSING

FIELD OF THE INVENTION

The invention relates to implantable medical devices having a liquid crystal polymer housing, and more particularly to implantable medical devices having a hermetically sealed liquid crystal polymer housing.

BACKGROUND OF THE INVENTION

Implantable medical devices (IMDs) are known and have been used for therapeutic and functional restoration indications for animals, including humans, for a number of years. These IMDs must be constructed in such a way that produces a hermetically sealed housing or case and of a material that is biocompatible. Ceramics, epoxies, and metals, such as titanium or titanium alloys have been the mainstay for many IMDs, including implantable pulse generators, pacemakers, and drug delivery pumps, for example.

A new class of material, known as thermoplastic liquid crystal polymers (LCP) have a unique combination of properties that make it well suited for encasing IMDs. LCP is extremely inert in biological environments and has barrier properties an order of magnitude greater than epoxy plastic materials and is virtually impermeable to moisture, oxygen, and other gases and liquids. The permeability of LCP to water vapor and to oxygen is close to that of glass. Sealed LCP enclosures have been tested and have passed initial hermeticity helium leak testing, per MIL-STD-883D.

LCP combines the low cost and light weight of a polymer with suitable dielectric properties and protective capabilities. High frequency performance is possible because of the dielectric constant and loss properties of LCP are much lower than those of conventional materials.

LCP can be precision molded and sealed using conventional thermoplastic welding techniques to create a hermetic seal. LCP is also readily processed by injection molding and thermoforming using conventional equipment at fast speeds with excellent replication of mold details, making a wide variety of shapes and configurations now more feasible. LCP packaging may also be laser welded at the bond line using infrared (IR) laser to create the seal. The LCP material is transparent to IR, so the beam passes through the LCP material with minimal absorption. An IR-absorbant material may be added to the LCP at the bond line, localizing heating to the immediate seal area. The welded seal is formed from the LCP material.

Implantable medical devices, such as an implantable pulse generator (IPG), typically include a hermetically sealed titanium case containing a power source and associated circuitry and glass filled conductor feed-thrus to allow the electronic signals generated by the circuitry to interface to a lead and electrode, sensor, and/or antenna, for example. Manufacturing is made more difficult because the glass filled feed-thrus must be welded to the housing in order to maintain a hermetic seal. The feed-thru locations are also restricted by the manufacturing and hermetic sealing requirements. The size of the IMD is generally dominated by the size of the power source and manufacturing limitations, and typically the titanium case ends up being at least a few centimeters in diameter and half a centimeter thick.

Many IMDs also include a rechargeable power source, such as a Litium Ion cell (battery), and a power receive coil for recharging the battery through a Radio Frequency (RF) magnetic field (or the like) generated outside the body. When these IMD's are encased in metal, the titanium acts as a shield, and reflects or absorbs much of the energy intended to recharge the internal battery. The internal power receive coil also needs to be large enough to receive the radio frequency (RF) magnetic field energy through the metal case, which also affects the size of the IMD.

Implant depth of the IMD is also affected by the case material. If it is too deep, the metallic case creates so much shielding that the recharge signal energy is unable to provide adequate recharging. Increasing the frequency of the recharge signal increases the blocking effect of the case which in turn results in an increase in heat produced by the case. On average, the RF magnetic field energy generated externally needs to be ten times greater than the necessary RF magnetic field energy received by the receive coil for adequate recharging, due in large part to the losses created by the titanium case.

IMDs may also incorporate wireless telemetry to provide remote control and programming features. The inclusion of a UHF antenna for the wireless telemetry outside the titanium case is necessary as the shielding offered by the titanium case will severely limit (effectively eliminate) radio wave propagation through the case. The antenna connection will be made through a feed-thru similar to that used for the lead connections. Alternatively, the wireless telemetry signal may be coupled inside the IMD onto a stimulus output channel and coupled to the antenna with passive filtering/coupling elements/methods.

FIGS. 1A and 1B show a typically IMD 20 and associated components. A metallic clam shell type housing (i.e., case) having a top half 22 and a bottom half 23, is provided to house the circuitry 24 and power source 26. One or more feed-thrus 28 are welded to the top half 22 and/or bottom half 23 (see FIG. 1B). A header 30 is typically coupled to the housing 22, 23, and feed-thrus 28 to provide an electrical connection point for the components not in the metallic housing (e.g., leads 32, electrodes 34, sensors 36, and/or antenna 38). The need to weld the feed-thrus 28 to the housing 22, 23 and couple the header 30 to the housing are both difficult manufacturing steps, and both create failure points, not to mention added expense to the manufacturing process. The IMD 20 is then subjected to a vacuum bake-out and then backfilled with an inert gas and the housing top half 22 and bottom half 23 are welded to produce a hermetically sealed device.

There remains a need for an improved IMD that can be constructed in a case (i.e., encased) that offers the liquid impermeability features of conventional materials, but also includes improved features, such as simpler manufacturing and less unwanted shielding, which will allow for a smaller and less expensive IMD that can be physically located in a wider range of areas within the body.

SUMMARY OF THE INVENTION

An improved IMD encased in LCP and having lower costs in manufacturing, and able to provide the flexibility to reduce the size of the external charger and implanted receive coil. The IMD can be deeper, smaller, and charging time to be less, and can be anywhere in the body where implantable circuitry with a power supply that needs recharging and/or communication is desired.

One aspect of the invention provides an implantable medical device having a liquid crystal polymer (LCP) housing. Circuitry is positioned within the housing to perform a predefined function, such as generate a stimulation waveform, or pump a fluid, or turn on a motor, for example. The circuitry may include a power source, and the power source may be a primary power source or a rechargeable power source.

The implantable medical device circuitry may also include a receive coil to receive externally generated power from an external power transmitter, the received power being used to recharge the rechargeable power source. The externally generated power may be no more than two times the magnitude of the power received by the receive coil.

Another aspect of the invention provides an implantable medical device comprising a molded liquid crystal polymer housing having at least two housing components, the housing components defining a pocket, and the housing components having an exterior surface. Circuitry positioned within the pocket to perform a predefined function, the circuitry including a power source, and at least one connection point accessible from the exterior of the housing, the connection point for electrically coupling an operative element to the circuitry positioned within the pocket. The power source may be a primary power source or a rechargeable power source.

Another aspect of the invention provides an implantable medical device comprising a molded liquid crystal polymer (LCP) structure, at least one conductive wire integrally molded within the LCP structure, and an operative element housed within the LCP structure, the operative element being electrically coupled to the at least one conductive wire. The LCP structure is sized and configured to be implanted within tissue or bone and is sealed to prevent the ingress of moisture. The operative element may be a circuit or battery or pump or motor. The conductive wire may include no treatment or is roughed-up or is pretreated with LCP, or glass, or ceramic, or another hermetic material.

Yet another aspect of the invention provides a method of manufacturing an implantable medical device comprising molding liquid crystal polymer (LCP) into a first housing component, molding LCP into a second housing component, molding at least one conductive wire through either the first housing component or the second housing component, or both, inserting an operative element into either the first housing component or the second housing component, the operative element being electrically coupled to the at least one conductive wire, sealing the first housing component to the second housing component to produce a LCP housing that is resistant to the ingress of moisture, and implanting the sealed housing within tissue or bone. The operative element may be a circuit or battery or pump or motor. The operative element may also include a rechargeable battery and a receive coil, the receive coil sized and configured to receive externally generated power to recharge the rechargeable battery.

Yet another aspect of the invention provides a kit of devices for use of an implantable medical device comprising a stimulation electrode sized and configured to be implanted in a targeted tissue region, an implantable medical device housed in liquid crystal polymer, a lead to couple the stimulation electrode to the implantable medical device, and instructions for use of the implantable medical device. The instructions may also include instructions for implanting the stimulation electrode in a targeted tissue region, coupling the stimulation electrode to the implantable medical device via the lead, and stimulating the targeted tissue region by conveying electrical stimulation waveforms from the implantable medical device to the stimulation electrode.

BRIEF DESCRIPTION OF THE DRAWINGS

FIG. 8A is a sectional view taken along lines 8A-8A in FIG. 7, showing a conductor passing through the LCP material with no conductor or LCP treatment.

FIG. 8B is a sectional view taken along lines 8B-8B in FIG. 7, showing a conductor passing through the LCP material with a roughed up conductor surface.

FIG. 8C is a sectional view taken along lines 8C-8C in FIG. 7, showing a conductor passing through the LCP material with a pretreatment of bonded LCP material.

FIG. 9 is a perspective view of the header and the circuitry configured for soldering the header and power source to the circuitry.

FIG. 10A is a perspective view of the implantable medical device of FIG. 2, showing a getter ready to be positioned with the pocket in the base, along with the circuitry.

2, showing a variety of possible shape configurations for position anywhere within the body.

Figure 1A:
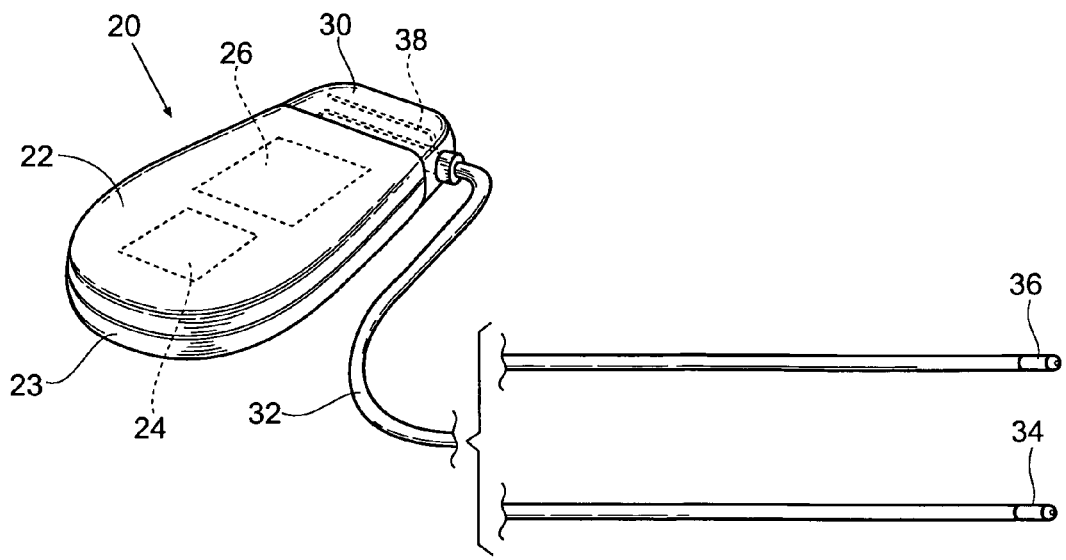
FIG. 1A is a perspective view of a typical implantable medical device encased in conventional materials, and coupled to operative components.
Figure 1B:
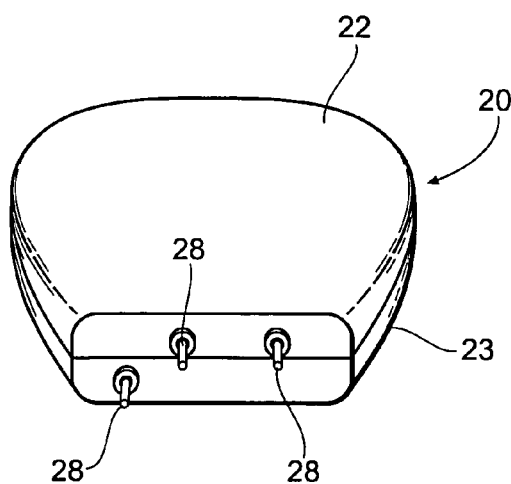
FIG. 1B is a perspective view of the implantable medical device shown in FIG. 1A, and showing one or more feed-thrus welded to the metallic case.
Figure 2:
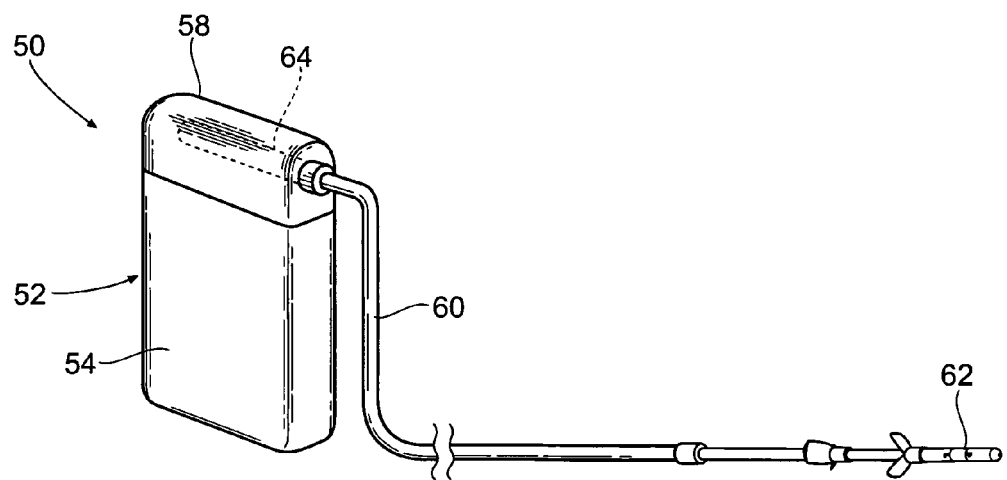
FIG. 2 is a perspective view of an implantable medical device of the present invention encased in a liquid crystal polymer (LCP) material, and coupled to an operative component.
Figure 25:
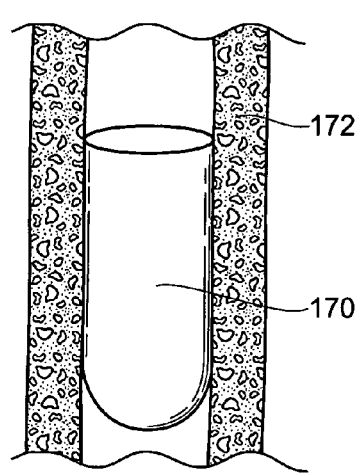

FIG. 25 is a perspective view of an alternative embodiment of the implantable medical device shown in FIG. 2, showing the implantable medical device positioned with a bone or other vessel.

Figure 26:
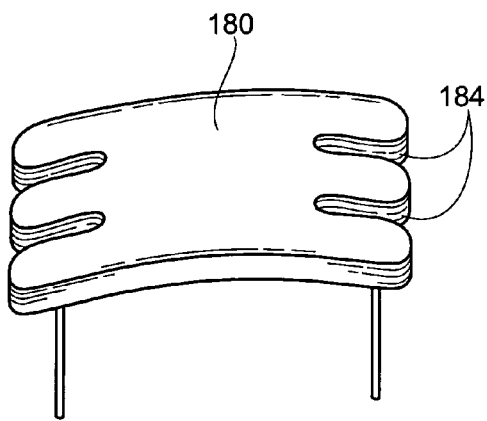
Figure 27:
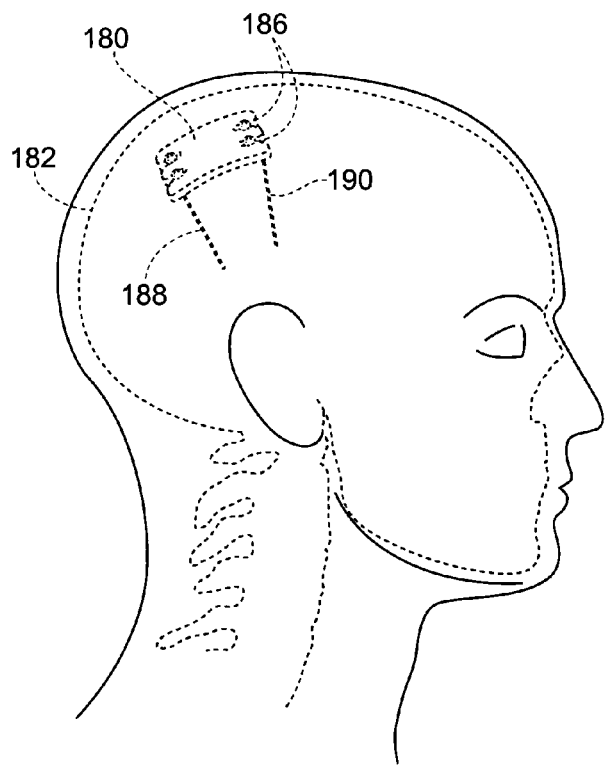
Figure 28:
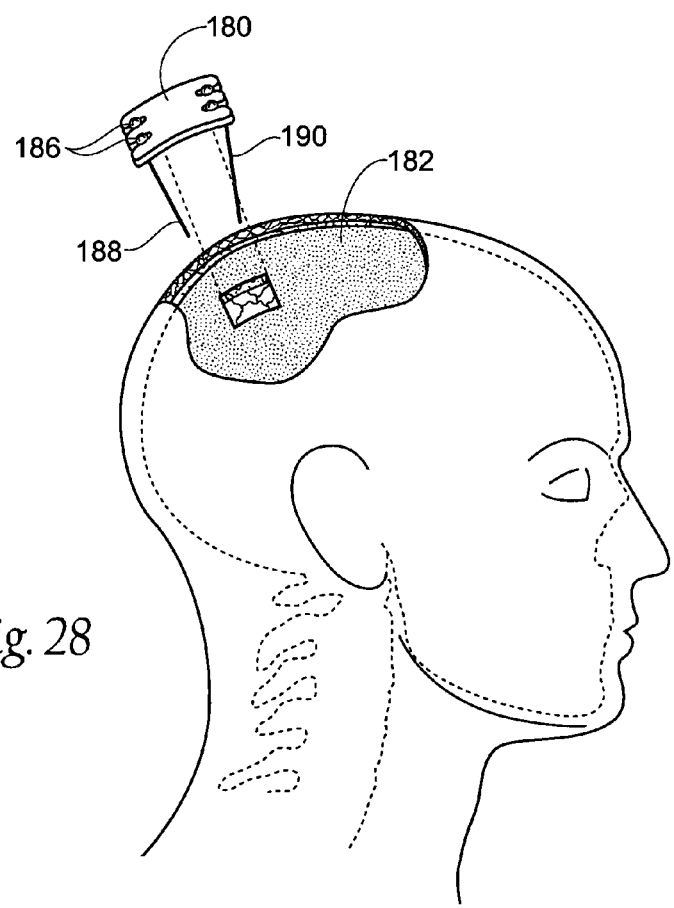

FIGS. 26 to 28 are perspective views of an alternative embodiment of the implantable medical device shown in FIG. 2, showing an implantable medical device sized and configured to be secured to the skull.

Figure 29:
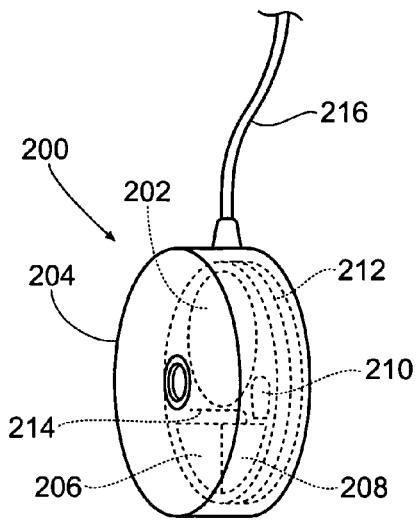
Figure 30:
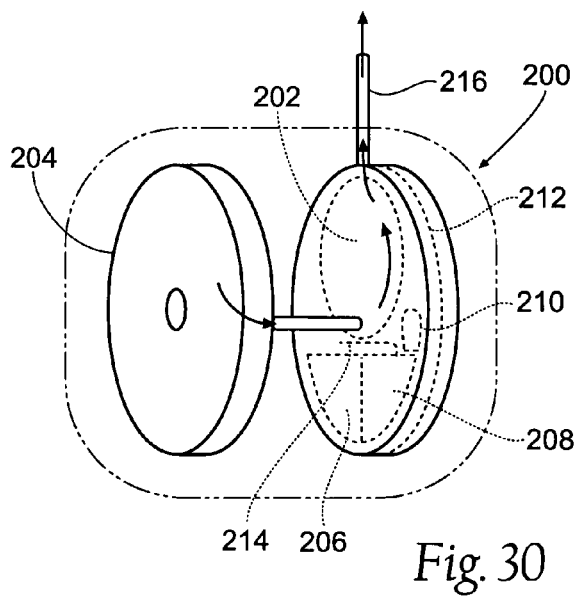
Figure 31:
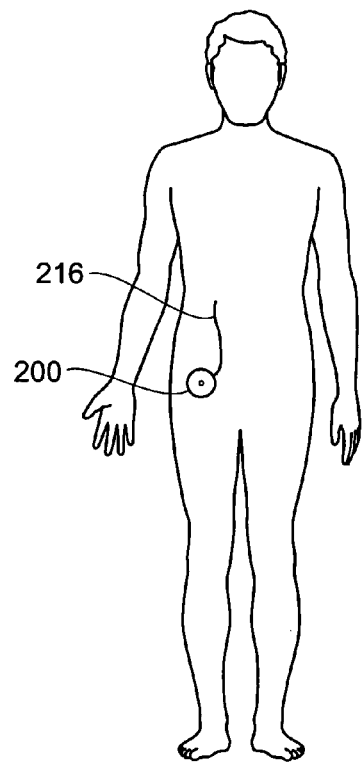

FIGS. 29 to 31 show views of an alternative embodiment of the implantable medical device shown in FIG. 2, showing a fluid pump or fluid circuit for delivery of a fluid to a targeted site.

Figure 32:
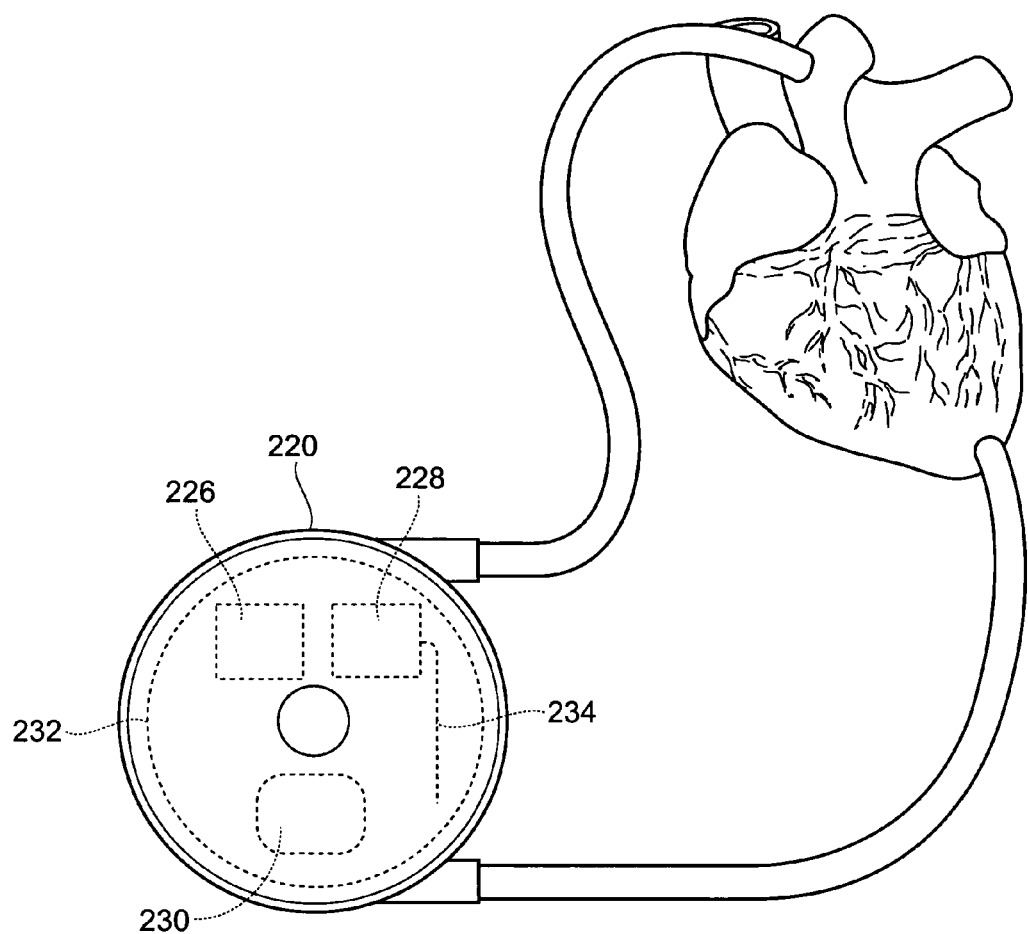

FIG. 32 is a diagrammatic view of an alternative embodiment of the implantable medical device shown in FIG. 2, showing a heart assist mechanism in fluid communication with the heart to assist with the pumping of blood.

FIGS. 33 to 35 are anatomical views of the implantable medical device shown in FIG. 2 implanted within a body to restore hand and/or arm function in patients with tetraplegia.

FIG. 36 is a plan view of a kit packaging the implantable medical device shown in FIG. 2 for use.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Liquid Crystal Polymer

Liquid crystal polymer (LCP) is so called because its molecules can be mutually aligned and organized (crystal), yet the bulk LCP can flow-(liquid) in the molten state. This behavior is unlike ordinary polymers that are randomly configured in the melt state or in the solution state. The liquid crystal state results from the rigid nature of segments of the LCP molecules. When the LCP flows in the liquid crystal state, the rigid segments of the molecules align next to one another in the shear flow direction, creating locally oriented domains. The domains in turn create macroscopic oriented regions. Once the oriented regions are formed, their direction and structure persist, even when the LCP approaches the melt temperature, because of the long relaxation time of the stiff chain LCP molecules.

Commercial LCPs are generally copolymers composed of molecules with rigid and flexible monomeric units. The ratio of the rigid monomer to the flexible monomer determines the properties of the LCP material. The high degree of molecular order that can be achieved with the LCP molecules at a supramolecular level results in a self-reinforced structure with outstanding strength, stiffness, and chemical barrier properties.

It is this unique combination of properties that make LCPs highly adaptable to IMD applications. For example, LCPs used in in-vivo environments have been shown to be biocompatible per USP (U.S. classification of medical grade materials). LCP has also been shown to have saline soak resistance with no evidence of degradation in mechanical properties being observed after five months in physiological saline solution. LCPs have not shown degradation in their mechanical properties during prolonged exposure to Ringer's solution. The barrier and dielectric properties of LCP materials is comparable to that of glass so that LCPs are virtually impermeable to moisture, oxygen, and other gases and liquids, and the maximum water absorption by LCPs is less than 0.02 percent. Electrical connection can be made through the LCP material without the need for welded feed-thrus or peripheral welds.

These unique properties make LCP materials an improvement over conventional materials used in the construction of IMDs. LCP is a unique material that satisfies the constraints of constructing IMDs where a hermetically sealed and sterile package is needed and size and placement issues are of importance. This makes LCP well suited for IMD encasement.

II. IMDs Encased in LCP

FIG. 2 shows an IMD, e.g., an implantable pulse generator (IPG) 50, incased in an LCP housing 52 having at least two housing components. The housing components include a base 54 having a pocket 56 (see FIG. 3), and a connection header 58 having a connector system 64 accessible from the exterior of the housing 52. The LCP header 58 is conventionally welded (i.e., laser, ultrasonic, IR) to the LCP base 54 to create a hermetically sealed IPG 50. An operative element, such as a lead 60 having an electrode 62 on its distal end, is shown coupled to the IPG 50 at the header 58. The electrode 62 is implanted in a targeted tissue region, and the lead 60 electrically couples the electrode to the IPG 50. The connector system 64 may be either custom components, or may be similar in design and construction to the low-profile IS-1 connector system (per ISO 5841-3). The IS-1 connectors have been in use since the late 1980s and have been shown to be reliable and provide easy release and re-connection over several implantable pulse generator replacements during the service life of a single lead. Full compatibility with the IS-1 standard is not a requirement for the IMD.

The IPG connection system may include a modification of the IS-1 connector system, which shrinks the axial length dimensions while keeping the format and radial dimensions of the IS-1. For application with more than two electrode conductors, the header 58 may incorporate one or more connection receptacles each of which accommodate leads with typically four conductors. When two or more leads are accommodated by the header, these lead may exit in a variety of configurations (e.g., from opposite sides of the header 58).

As will be described in greater detail later, the base 54 and/or the header 58 can take on any configuration, or the header 58 can be integral with the base 54, for example, to create a wide variety of alternative configurations for IMDs. Alternatively, the components of the implantable medical device could be integrally molded within LCP, as compared to positioned within a LCP housing.

These connectors can be similar to the banded axial connectors used by other multi-polar implantable pulse generators or may follow the guidance of the draft IS-4 implantable connector standard. The design of the IPG housing 52 and header 58 preferably includes provisions for adding larger headers for such indications.

Figure 3:
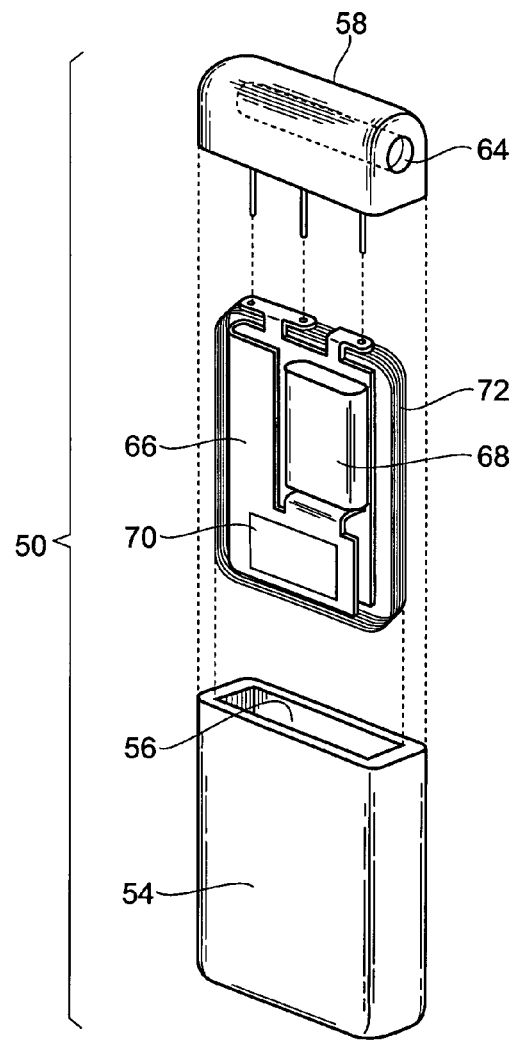
FIG. 3 is an exploded view of the implantable medical device shown in FIG. 2.

A circuit 66 for generating electrical stimulation waveforms is housed within the base 54 (as shown in FIG. 3) and/or header 58. An on-board, primary or rechargeable power source 68 (i.e., battery), desirably provides the power. The implantable pulse generator 50 also desirably includes an on-board, programmable microcontroller 70, which carries operating system code. The code expresses pre-programmed rules or algorithms under which the desired electrical stimulation waveforms are generated by the circuit 66. When a rechargeable power source is used, the circuitry 66 may also include a power receive coil 72 for recovery of externally generated power.

Instructions for use 260 may accompany the IMD 50 system. The instructions 260 may prescribe, but is not limited to, use of the IMD 50, including the use of the external controller 242 to operate the implanted medical device 50 (see FIG. 36).

A. Benefits from LCP

Construction of IMDs using LCP offer a number of benefits over conventional IMD materials. One important benefit of LCP over metals such as titanium is the greatly improved power transfer. With little or no interference or shielding caused by a metallic housing, a number of operative elements within the IMD housing may be reduced in size and the external charging device may also be reduced in size. These features create additional options in IMD design and a much smaller and more flexible IMD. With the same size receive coil, the IMD could recover the same power with less charging power, or the IMD could be implanted deeper (anywhere) within the body because it could recover more charging power, and the IMD could recharge faster, all because there is little or no metal interference.

The receive coil could also be made much smaller, to help reduce the IMD design. Instead of the necessity to size the receive coil based on its ability to recover only a fraction, e.g., 1/10th, of the generated power, the receive coil can now be sized based on its ability to recover a much larger portion of the generated power, e.g., perhaps over 50 percent. The greater ease of coupling power to recharge the battery may also allow a shorter period of charging. This may also allow the use of a smaller battery that is recharged more frequently by the user.

Without a metal housing to prevent RF signals from reaching the circuitry, there may need to be some internal shielding from RF interference for the circuitry. This also eliminates the need for an additional feed-thru for an antenna to exit the metal housing of a traditional IMD, which simplifies manufacture and saves cost.

These features provide an improved IMD having lower costs in manufacturing, and provide the flexibility to reduce the size of the external charger and implanted receive coil. The IMD can be deeper, smaller, and charging time to be less, and can be anywhere in the body where implantable circuitry with a power supply that needs recharging and/or communication is desired.

B. IMD Construction

Figure 4:
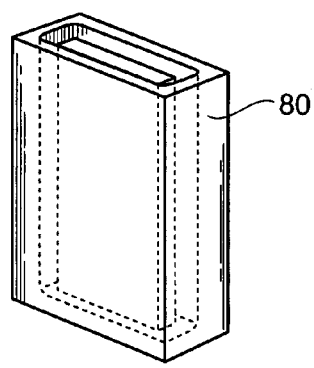
FIG. 4 is a perspective view of a possible mold for the base of the implantable medical device shown in FIG. 2.
Figure 5:
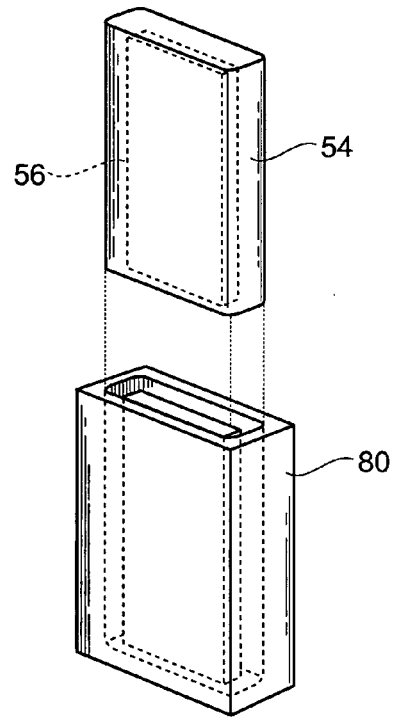
FIG. 5 is a perspective view of the molded LCP base removed from the mold shown in FIG. 4.
Figure 6:
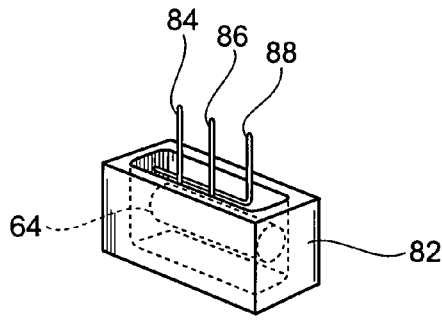
FIG. 6 is a perspective view of a possible mold for the header of the implantable medical device shown in FIG. 2.
Figure 7:
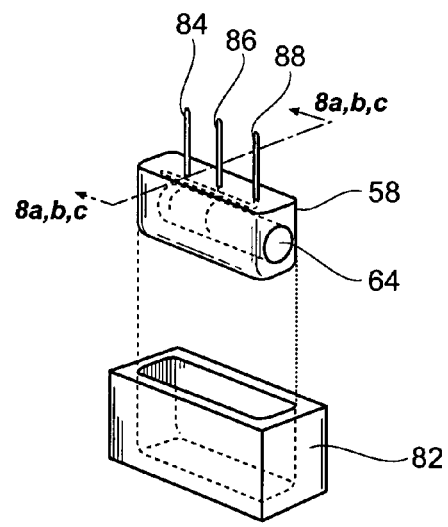
FIG. 7 is a perspective view of the molded LCP header removed from the mold shown in FIG. 7.

To create the base 54 and header 58, molds are made for the desired configuration of the IPG 50. FIGS. 4 and 5 show a mold 80 used to produce the base 54. The LCP material is poured into the mold 80, and allowed to cure. The base 54 is then removed from the mold 80 (see FIG. 5). As shown in FIGS. 6 and 7, mold 82 may be used to create the header 58. Receptacle 64 and associated conductors 84, 86, 88 are held in the mold using conventional molding techniques, e.g., offset pins, a vacuum, or implantable safe adhesives. The mold 82 is then filled with LCP, and allowed to cure. The header 58 is then removed from the mold 82 (see FIG. 7). As previously described, there is no need for laser welding of feed-thrus to the housing. The antenna for the wireless telemetry may be located in the header 58, in the base 54, or with the circuitry 66.

Once each mold is complete, the base and header can be produced at a high speed and with constant production tolerances. In addition, the flexibility of LCP molding can provide an infinite number of shapes for both the base and header, and provides more options for connection points/locations.

As shown in FIG. 7, conductors 84, 86, 88 pass through the molded LCP header 58. FIGS. 8A to 8C show possible conductor configurations for the conductor to LCP interface 90. This interface or bond between the metal conductor 84 and LCP material 92 may provide a possible source of moisture infiltration, so care must be taken to adhere or seal the conductor 84 to the LCP material 92. (This is true for all conductors passing through the LCP material.)

FIG. 8 shows a representative conductor 84 passing through the LCP 92 without any conductor or LCP treatment. This configuration may allow for a small amount of moisture infiltration at the conductor to LCP interface 90. FIG. 8B shows the conductor 84 having a roughed up surface 94 (i.e., small protuberances and/or depressions, or micro or macroscopic etching, for example) to provide an increased surface area to help adhere the conductor 84 to the LCP 92 and to improve the seal. FIG. 8C shows the conductor 84 having been pretreated with a chemical or vapor deposition to bond LCP material 96 (or a derivative LCP) to the conductor 84. Alternatively, the coating applied to the conductor 84 prior to molding in LCP may be a glass or ceramic or other non-moisture permeable material. The LCP 96 covered conductor 84 is then molded in the LCP material 92, causing the LCP 96 deposited on the conductor 84 to bond with the LCP material 92 to provide the seal.

As can be seen in FIG. 9, the conductors 84, 86, 88 of header 58, and the power source 68, may then be coupled, e.g., soldered, to the IPG circuitry 66. The circuitry 66 may then be positioned within the pocket 56 in the base 54. A "getter" 102 may also be inserted into the pocket 56 to absorb any water vapor or other undesirable vapors that may permeate the LCP material (see FIG. 10A).

Figure 10B:
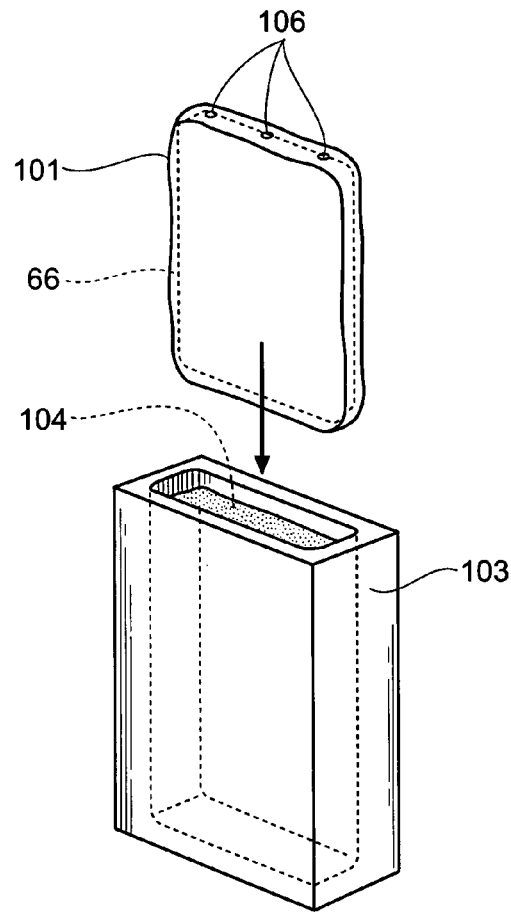
FIG. 10B is a perspective view of the circuitry covered in a protective blanket prior to being dipped in LCP material.
Figure 10C:
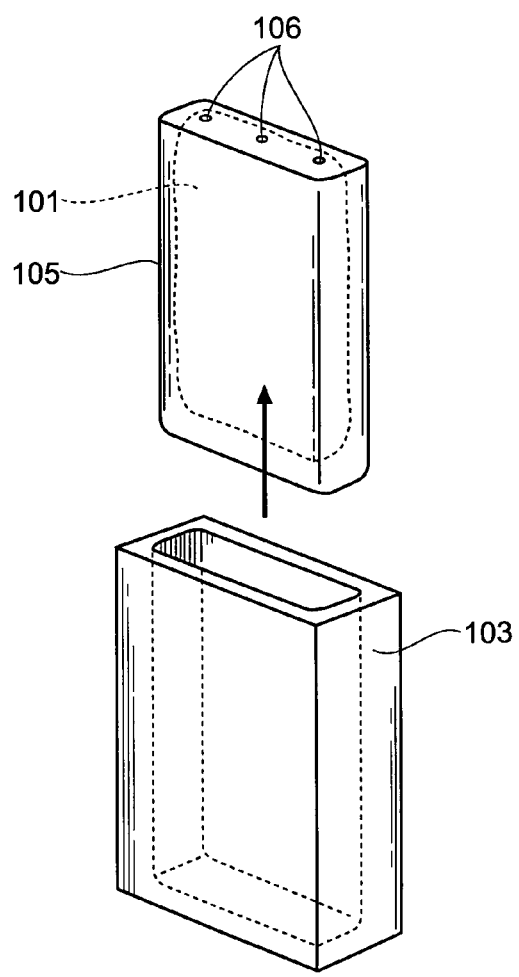
FIG. 10C is a perspective view of the circuitry and molded LCP removed from the mold shown in FIG. 10B.
Figure 10D:
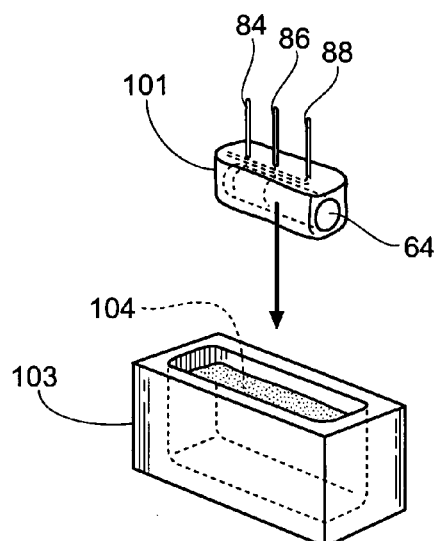
FIG. 10D is a perspective view of the header components covered in a protective blanket prior to being dipped in LCP material.
Figure 10E:
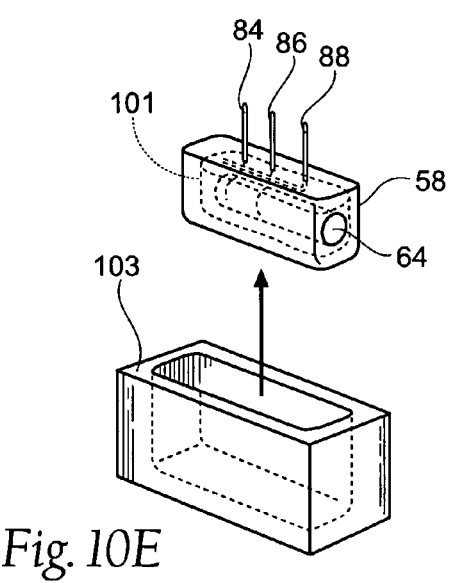
FIG. 10E is a perspective view of the header components and molded LCP removed from the mold shown in FIG. 10D.
Figure 10F:
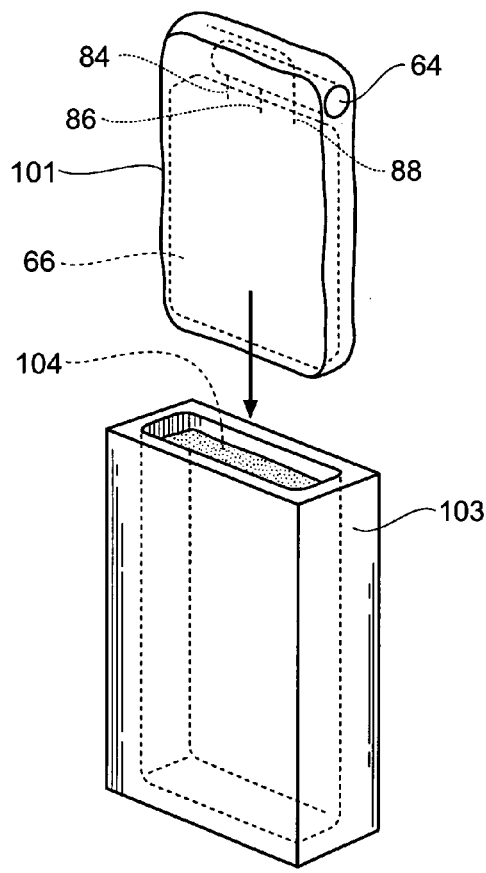
FIG. 10F is a perspective view of the circuitry combined with the header components covered in a protective blanket prior to being dipped in LCP material.
Figure 10G:
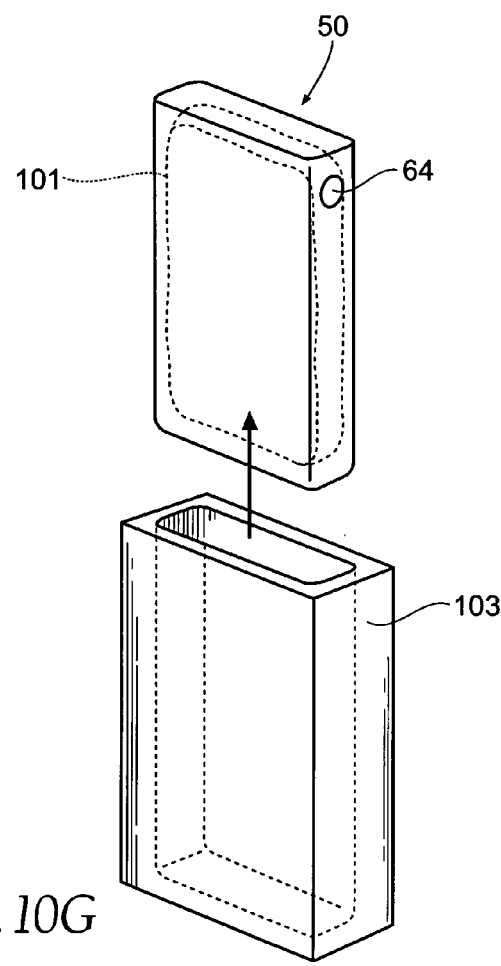
FIG. 10G is a perspective view of the combined circuitry and header components molded LCP removed from the mold shown in FIG. 10F.
Figure 11:
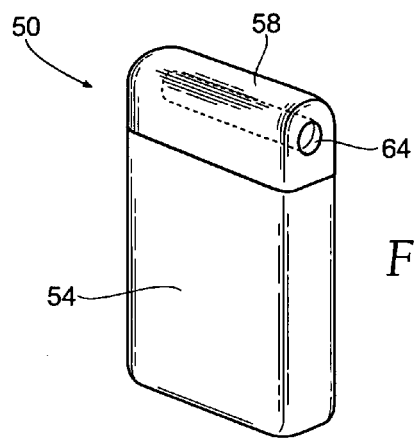
FIG. 11 is a perspective view of the implantable medical device of FIG. 2 prior to bake-out and welding.

In an alternative embodiment, the circuitry 66, battery 68, microcontroller 70, and receive coil 72, or portions thereof, may be covered with a thermal blanket 101. The thermal blanket covering 101 serves to provide thermal protection for the circuitry and any other components from contact with high temperatures from the molten LCP. The covered circuitry may then be completely molded within molten LCP material. Apertures 106 could be maintained to allow coupling of the circuitry 66 to the header 58. FIG. 10B shows a mold 103 partially filed with molten LCP material 104. The mold 103 can take any desired shape. The covered circuitry may first be pre-cooled, and then dipped into the LCP material 104, and the LCP allowed to cure. The circuitry molded in the LCP 105 is then removed from the mold 103 (see FIG. 10C). The header 58 (i.e., receptacle 64 and associated conductors 84, 86, 88), could be assembled and molded in LCP in the same manner (see FIGS. 10D and 10E), and then coupled to the circuitry molded in the LCP 105 (see FIG. 11), or the components of the header 58 could be coupled to the circuitry 66 and the combination dipped, or pre-cooled and dipped into LCP material to create an IPG 50 molded in LCP (see FIGS. 10F and 10G).

Figure 12:
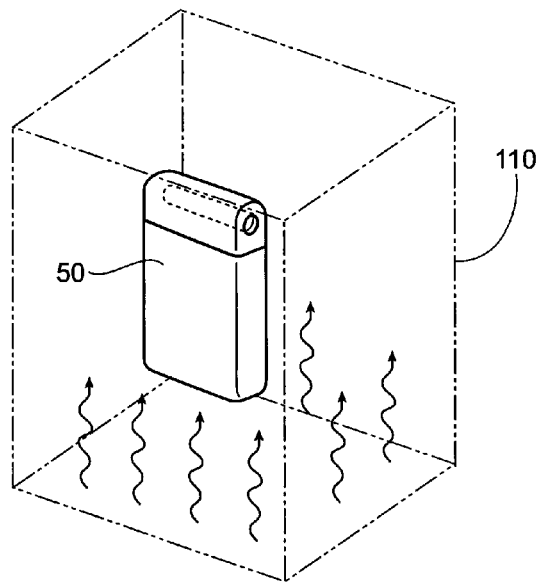
FIG. 12 is a perspective view of the implantable medical device shown in FIG. 2 during the bake-out process.
Figure 13:
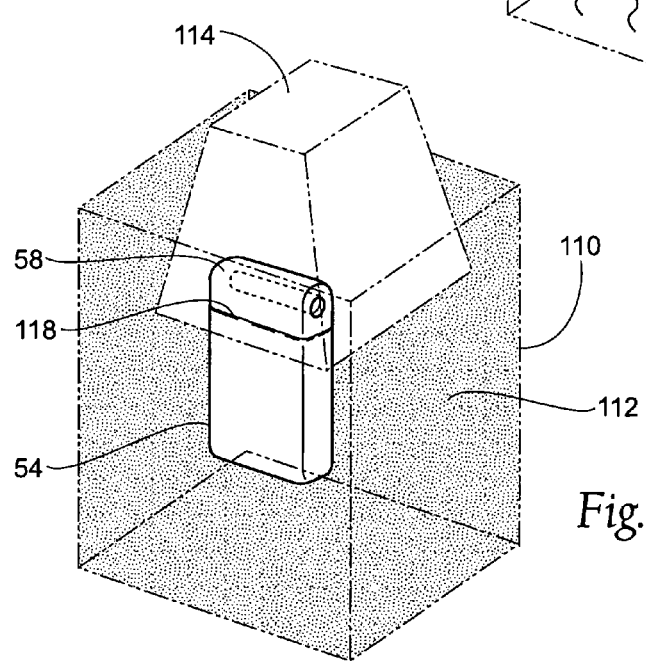
FIG. 13 is a perspective view of the implantable medical device shown in FIG. 2 during the backfill and welding process.
Figure 14:
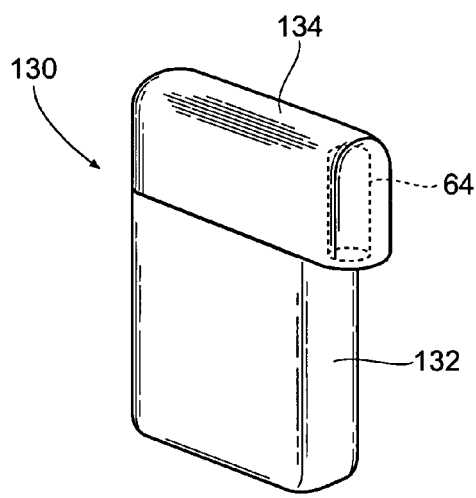
FIGS. 14 to 17 are perspective views of a variety of header configurations.
Figure 15:
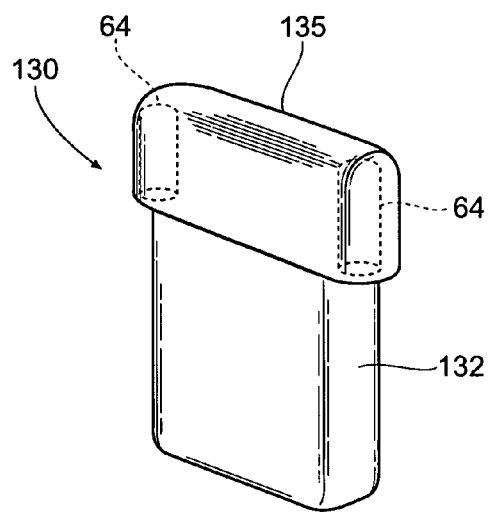
Figure 16:
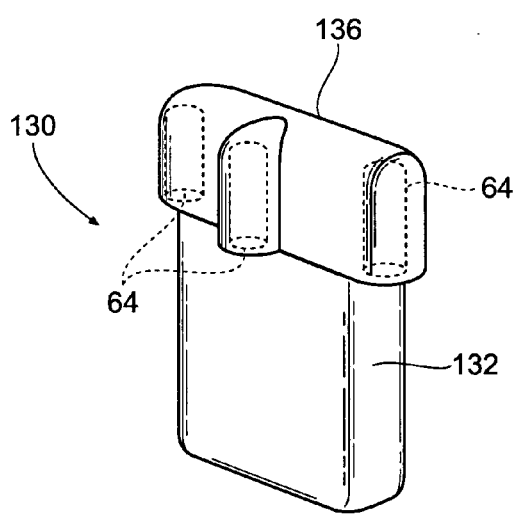
Figure 17:
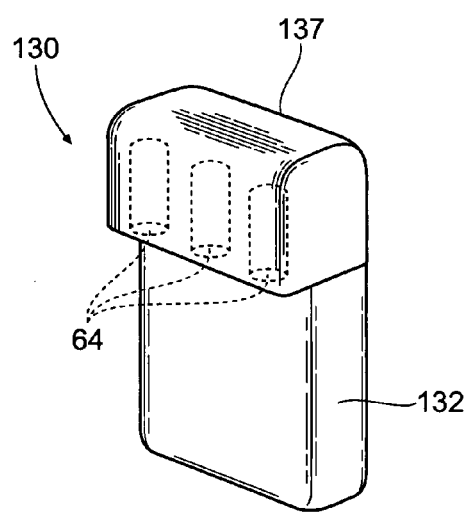

The assembled IPG 50 (see FIG. 11) is then subjected to a vacuum bake-out process in chamber 110 (see FIG. 12). The vacuum bake-out process drives out any moisture content within the unsealed IPG 50 and burns off any other volatile contaminants in preparation for the final sealing of the IPG 50. After a predetermined bake-out period (e.g., about 45 degrees Celsius to about 100 degrees Celsius, and for about 24 to about 48 hours), the chamber 110 is then backfilled with an inert gas or gas mixture 112, such as helium-argon (see FIG. 13), until the inert gas 112 occupies all the free space within the IPG 50. As shown in FIG. 13, welding means, such as an ultrasonic weld horn 114, may be used to ultrasonically weld the base 54 to the header 58 at the seam 118 where the base 54 and header 58 come together. The ability to use a weld horn 114 also improves to production speed. An ultrasonic pinpoint beam may also be used in place of the weld horn 114.

Alternative welding methods include laser or solvent bonding. A hermetically sealed IPG 50 is produced and may be sterilized prior to use.

III. Alternative IMD Configurations

As previously described, the manufacturing flexibility of LCP allows for a wide variety of shapes and configurations for IMDs that have not been possible with other IMD housing materials. For example, FIGS. 14 to 17 show an IMD 130 with multiple header configurations. The LCP provides greater flexibility to connection options, as shown, which in turn provides a wider range of anatomical placement options within the body. The base configuration 132 can remain the same, while allowing for unlimited header configurations 134, 135, 136, 137. The lead, or multiple leads, can be coupled to the receptacle(s) 64 in the headers 134, 135, 136, 137 in a parallel or perpendicular path out of the IMD 50 (or any other desired path). This allows for bends in lead at or near the connection point to be reduced or eliminated.

Figure 18:
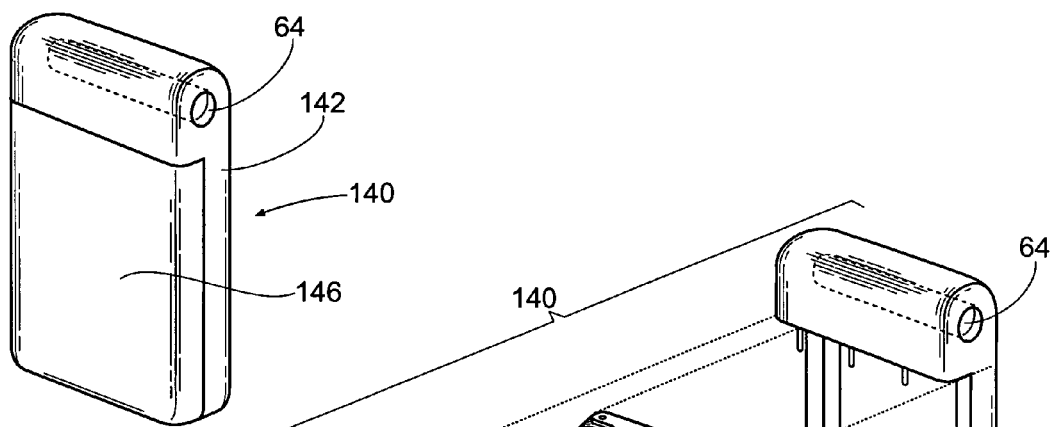
FIGS. 18 and 19 are perspective views of an alternative embodiment of the implantable medical device shown in FIG. 2, showing a combined base and header, the implantable medical device having a pocket and a lid to seal the implantable medical device.
Figure 19:
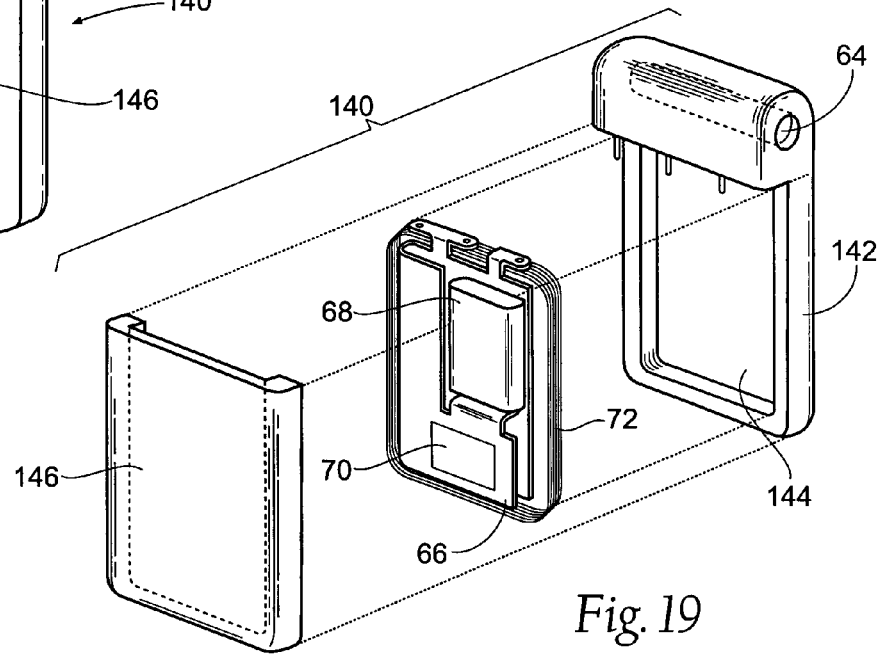
Figure 20:
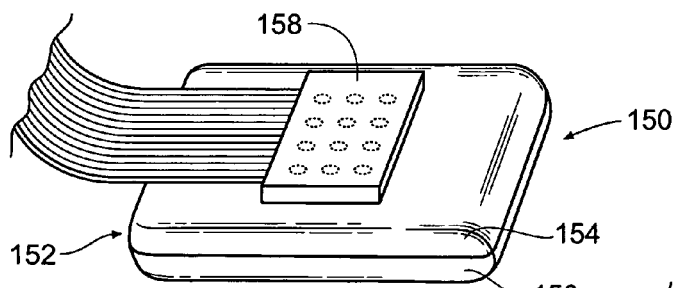
FIGS. 20 and 21 are perspective views of an alternative embodiment of the implantable medical device shown in FIG. 2, showing a connection system for multi-lead applications.
Figure 21:
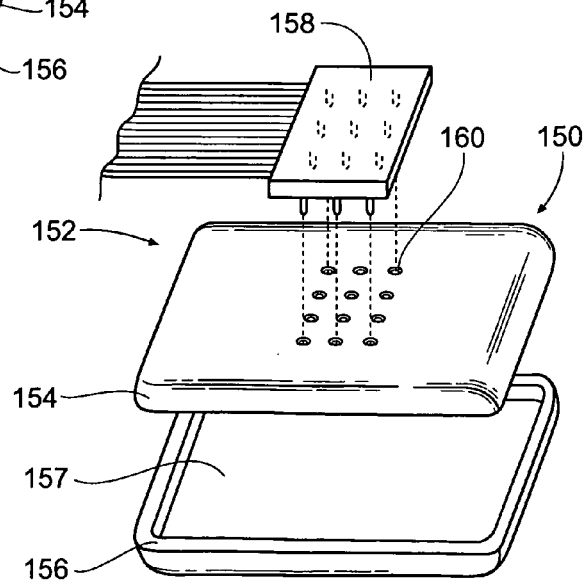

In addition to alternative header configurations, the IMD 140 may comprise a combined base and header 142 having a pocket 144 and a lid 146 (see FIGS. 18 and 19). FIGS. 20 and 21 show and IMD 150 with a multiple connection system for multi-lead applications. In this configuration, the base 152 comprises a top shell 154 and a bottom shell 156, which form a pocket 157 for the IMD circuitry. A multi-lead connector 158 can be coupled to a multi-lead receptacle 160 molded into the top shell 154 (as shown) or bottom shell 156. This type of connection system for multi-lead applications provides flexibility and allows for multiple connections in a small dimensioned package.

Figure 22:
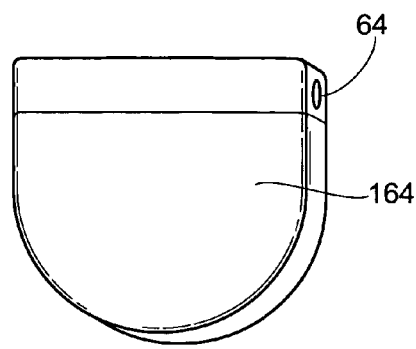
FIGS. 22 to 24 are perspective views of an alternative embodiment of the implantable medical device shown in FIG.
Figure 23:
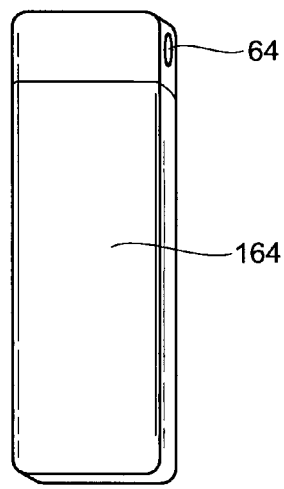
Figure 24:
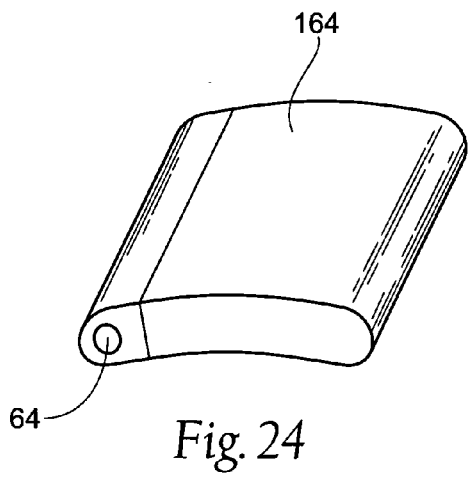

FIGS. 22 to 26 show a variety of shapes for anatomical position virtually anywhere within the body to fit specific applications. FIGS. 22 to 24 show the general flexibility in IMD shapes. Each IMD includes an LCP housing 164 having an internal space for circuitry, and at least one receptacle 64 to couple the internal IMD circuitry with an operative element, such as a lead, electrode, and/or sensor. FIG. 25 shows a round or tubular shaped IMD 170 sized and configured to be positioned within a bone 172 to aid in controlling bone growth, for example.

FIGS. 26 to 28 show an IMD 180 sized and configured to be fastened to the skull 182 for cortical stimulation or deep brain stimulation applications, for example. The IMD 180 may be curved to match the curvature of the skull 182, and may include securing means, such as apertures or recessed portions 184, to allow a screw or screws 186 to secure the IMD 180 to the skull 182. The IMD 180 is shown with two leads 188, 190, although any number of leads could be coupled to the IMD.

FIGS. 29 to 31 show an IMD 200 sized and configured as a fluid pump or fluid circuit. The fluid pump 200 may be encased in LCP, or only a portion or portions may be encased in LCP. The fluid pump 200 may include a pump 202 in fluid communication with a fluid reservoir 204. A power source 206 powers circuitry 208 and a motor 210. A receive coil 212 may also be included if the power source 206 is rechargeable. An antenna 214 may be included for wireless telemetry. The circuitry 208 determines when to power the motor to deliver fluid to a targeted site through a fluid delivery tube 216. The fluid pump 200 would be implanted near the skin so that when the reservoir 204 needed refilling, a needle could be inserted transcutaneously into the reservoir for refilling.

FIG. 32 shows a heart assist device 220. The assist device 220 serves to take over the majority of the heart's pumping function and allow the heart to rest, heal, and grow stronger. As a result, patients often become healthier and stronger before they undergo transplant surgery. The heart assist device 220 may be encased in LCP, or only a portion or portions may be encased in LCP. A power source 226 powers circuitry 228 and a pump motor 230. A receive coil 232 may also be included if the power source 226 is rechargeable. An antenna 234 may be included for wireless telemetry.

FIGS. 33 to 35 show the use of an IPG 240 to restore hand and/or arm function in patients with tetraplegia. The IPG 240 can be used to control one arm, as shown in FIG. 33, or to control both arms, as shown in FIG. 34. FIG. 35 shows the use of the IPG 240 to restore hand grasp functionality. The IPG 240 may include one or more leads 244 (two leads are shown) extending into one or both arms to deliver a stimulation waveform. A controller 242 may be used by the patient to initiate the stimulation waveforms from the IPG 240 to stimulate muscles within the arm. It is to be appreciated that more than one IPG may be incorporated into a system to restore function in patients with spinal cord injuries. Shoulder or wrist sensors may also be included and may use telemetry to transmit data to the IPG 240.

FIG. 36 shows a representative kit 250 for carrying out an implant procedure for an implantable medical device 50. The kit 250 may include the implantable medical device 50, the implantable lead 60 and electrode 62, and an external controller 242. The kit 250 may also include a surgical tool system 252, which may comprise a needle 254, sleeve 256, and tunneling tool 258. The instructions 260 for use in the kit 250 direct use of these instruments to implant the lead 60 and electrode 62, form a subcutaneous pocket, tunnel the lead 60, and implant the medical device 50 in the subcutaneous pocket. The instructions 260 for use can also direct use of the implantable medical device 50, use of the external controller 242 to operate the implanted medical device 50, as well as use of a clinical programmer to program the implanted medical device 50.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An implantable medical device comprising:
an outer housing comprising a liquid crystal polymer; and
circuitry positioned within the outer housing to perform a predefined function, wherein the circuitry includes a power source and wireless telemetry circuitry.

2. The device of claim 1, wherein the power source comprises a rechargeable power source.

3. The device of claim 2, wherein the circuitry further includes a receive coil to receive externally generated power from an external power transmitter, and wherein the received power recharges the rechargeable power source.

4. The device of claim 3, wherein the externally generated power is no more than two times the magnitude of the power received by the receive coil.

5. The device of claim 1, the circuitry further including a microcontroller.

6. The device of claim 5, wherein the microcontroller carries operating system code, and wherein the operating system code expresses pre-programmed rules or algorithms under which the predefined function is generated by the circuitry.

7. The device of claim 1, wherein the wireless telemetry circuitry further includes an antenna.

8. The device of claim 1, wherein the predefined function is to generate a stimulation waveform, or to turn on a pump, or to turn on a motor.

9. An implantable medical device comprising:
a liquid crystal polymer outer housing having at least two housing components, the housing components defining a pocket, wherein the housing components comprise an exterior surface;
circuitry positioned within the pocket to perform a predefined function, wherein the circuitry includes a power source and wireless telemetry circuitry; and
at least one connection point accessible from the exterior of the outer housing, wherein the connection point is configured to electrically couple an operative element to the circuitry positioned within the pocket.

10. The device of claim 9, wherein the power source comprises a rechargeable power source.

11. The device of claim 10, wherein the circuitry further includes a receive coil to receive externally generated power from an external power transmitter, and wherein the received power recharges the rechargeable power source.

12. The device claim 11, wherein the externally generated power is no more than two times the magnitude of the power received by the receive coil.

13. The device of claim 9, the circuitry further including a microcontroller.

14. The device of claim 13, wherein the microcontroller carries operating system code, and wherein the operating system code expresses pre-programmed rules or algorithms under which the predefined function is generated by the circuitry.

15. The device of claim 9, wherein the wireless telemetry circuitry further includes an antenna.

16. The device of claim 15, wherein the antenna is contained within the pocket within the liquid crystal polymer outer housing.

17. The device of claim 9, wherein the predefined function is to generate a stimulation waveform, or to turn on a pump, or to turn on a motor.

18. An implantable medical device comprising
an outer housing comprising a liquid crystal polymer (LCP) structure,
at least one conductive wire integrally molded within the LCP structure,
an operative element housed within the LCP structure, the operative element being electrically coupled to the at least one conductive wire and further comprising circuitry configured to generate a stimulation waveform, a pump or a motor, and
circuitry positioned within the outer housing, the circuitry including a power source.

19. The device of claim 18, wherein the operative element further comprises a battery.

20. The device of claim 18, wherein the at least one conductive wire includes no treatment or is roughed-up or is pretreated with LCP, or glass, or ceramic, or another hermetic material.

21. A method of manufacturing an implantable medical device, the method comprising:
molding liquid crystal polymer (LCP) into a first housing component;
molding LCP into a second housing component;
inserting circuitry into the first housing component or the second housing component, wherein the circuitry includes a power source and wireless telemetry circuitry; and
sealing the first housing component to the second housing component to produce a LCP outer housing that is resistant to the ingress of moisture.

22. The method according to claim 21, further comprising:
molding at least one conductive wire through either the first housing component or the second housing component, or both; and
inserting an operative element into either the first housing component or the second housing component, the operative element being electrically coupled to the at least one conductive wire, wherein the operative element is comprises a circuit, a battery, a pump, or a motor.

23. The method according to claim 22, wherein the operative element includes a rechargeable battery and a receive coil, the receive coil being sized and configured to receive externally generated power to recharge the rechargeable battery.

24. A kit comprising
a stimulation electrode sized and configured to be implanted in a targeted tissue region,
an implantable medical device comprising:
an outer housing comprising a molded liquid crystal polymer; and
circuitry positioned within the outer housing to perform a predefined function, wherein the circuitry includes a power source and wireless telemetry circuitry;
a lead configured to couple the stimulation electrode to the implantable medical device, and
instructions for use of the implantable medical device.

25. The kit according to claim 24, the instructions further comprising instructions for implanting the stimulation electrode in a targeted tissue region, coupling the stimulation electrode to the implantable medical device via the lead, and stimulating the targeted tissue region by conveying electrical stimulation waveforms from the implantable medical device to the stimulation electrode.

* * * * *

UNITED STATES PATENT AND TRADEMARK OFFICE
CERTIFICATE OF CORRECTION

PATENT NO.        : 8,463,393 B2
APPLICATION NO.   : 11/473682
DATED             : June 11, 2013
INVENTOR(S)       : Strother et al.

Page 1 of 1

It is certified that error appears in the above-identified patent and that said Letters Patent is hereby corrected as shown below:

In the Claims

Column 11, line 41, claim 18: "An implantable medical device comprising an outer housing" should read -- An implantable medical device comprising: an outer housing --.

Column 12, lines 25-26, claim 22: "element is comprises" should read -- element comprises --.

Column 12, line 32, claim 24: "A kit comprising a stimulation" should read -- A kit comprising: a stimulation --.

Signed and Sealed this
Twenty-seventh Day of January, 2015

Michelle K. Lee
*Deputy Director of the United States Patent and Trademark Office*